(12) United States Patent
Mitomi (10) Patent No.: US 6,859,636 B2
(45) Date of Patent: Feb. 22, 2005

(54) IMAGE READING APPARATUS

(75) Inventor: Yuuichi Mitomi, Kofu (JP)

(73) Assignee: Nisca Corporation, Yamanashi-ken (JP)

( * ) Notice: Subject to any disclaimer, the term of this patent is extended or adjusted under 35 U.S.C. 154(b) by 364 days.

(21) Appl. No.: 09/986,473

(22) Filed: Nov. 8, 2001

(65) Prior Publication Data

US 2002/0143375 A1 Oct. 3, 2002

(51) Int. Cl.$^7$ .............................................. G03G 15/00
(52) U.S. Cl. ........................................ 399/367; 399/374
(58) Field of Search ............................... 399/367, 371, 399/372, 405, 361, 374, 17; 358/496

(56) References Cited

U.S. PATENT DOCUMENTS

| | | | | |
|---|---|---|---|---|
| 5,267,058 A | * | 11/1993 | Sata | 358/498 |
| 5,455,667 A | * | 10/1995 | Hiroi et al. | 399/373 |
| 5,995,801 A | * | 11/1999 | Katsuta et al. | 399/367 |
| 6,040,923 A | * | 3/2000 | Takashimizu et al. | 358/498 |
| 6,323,933 B1 | * | 11/2001 | Anzai | 355/23 |

FOREIGN PATENT DOCUMENTS

JP      62-179271      8/1987

OTHER PUBLICATIONS

Patent Abstracts of Japan, Publication No. 63–180650, Published on Jul. 25, 1988.
Patent Abstracts of Japan, Publication No. 11–032164, Published on Feb. 2, 1999.

* cited by examiner

Primary Examiner—Anthony H. Nguyen
(74) Attorney, Agent, or Firm—Manabu Kanesaka (57) ABSTRACT

Establishing a reading station for reading images on an document disposed in a transport path between paired transport rollers and paired discharge rollers to sequentially feed documents on a sheet supply tray enables a compact device and arranging a detection sensor that detects the trailing edge of an document to detect the discharge thereof to a discharge tray at a position on the discharge tray side from the pressing point of the paired discharge rollers, and the positioning of a detection sensor to detect the leading edge of an document to control the start of reading documents, at a position upstream of the transport roller prevents distortion of the document and enables the certain detection of documents.

7 Claims, 6 Drawing Sheets

IMAGE READING APPARATUS

BACKGROUND OF THE INVENTION and RELATED ART STATEMENT

This invention relates to an image reading apparatus for scanning and optically reading a document image and outputting electronic data. More particularly, this invention relates to a structure of an automatic document feeder for transporting documents to a determined reading station and for discharging documents.

Image reading apparatus optically read images on a document, convert the images to electronic data, and transmit that data to image forming apparatus, such as an external personal computer, a copier or a facsimile machine. Many image forming apparatus are equipped with such image reading apparatus.

Image reading apparatus are provided with a light source for irradiating light onto a document that is pulled out and transported by an automatic document feeder one at a time and image sensors that receive the light reflected from the surface of the document.

However, it has been demanded recently that the automatic document feeder apparatus disposed on image reading apparatus be compact, lightweight and comprise fewer parts. Such an improved apparatus disclosed in Japanese Patent Publication 62-179271 shows a structure that has discharge rollers immediately after the document reading station so that these discharge rollers discharge documents to a discharge tray. This apparatus shortens the path to transport documents, and due to a configuration using least minimum number of rollers required in the transport of the documents, the structure for the transport of documents can be compact, lightweight and has fewer parts.

This apparatus is provided with a detection means to detect documents between a reading position for reading documents and discharge rollers. In general, there are two types of detection means; a lever type sensor detection method (or a lever type sensor) detects a motion of a detection lever disposed in the transport path swung by a sheet of document; and a reflective type sensor detection method (or a reflective type sensor) detects an interruption of light caused by a sheet of document. The light is emitted from a light-emitting unit, and is configured to be reflected by a reflective plate and returned to a light reception unit.

However, when employing the former lever type detection method, having a detection means between the document reading station and the discharge roller causes a problem, where a shock of the document striking the lever distorts images while being read because the documents is in a free state when the edge of the document hits the lever.

In particular, when the image sensor is a contact image sensor (CIS) type using a SELFOC lens, not only distortion of the image but out-focus can occur since the focus depth of CIS type sensor is extremely shallow compared to a reduction type sensor.

Also, when the latter reflective type sensor is employed, the light generated by the light source for the reading means can be mistakenly detected.

Particularly, if the image sensor is a reduction type for reading images via a plurality of mirrors reflected from a document surface, there is a greater chance of such error due to higher intensity of light.

An object of the present invention is to provide a document reading apparatus that it will not create a shock to documents while being read even though a reading apparatus is compact and lightweight. Another object of the present invention is to provide a document image reading apparatus that prevents a detection error during document transportation and achieves reliable detection.

This invention comprises a transport path for sequentially feeding documents from a sheet supply tray, a reading station for reading images on the documents disposed in the transport path, a photoelectric conversion means for photoelectrically converting images on documents moving over the reading station, a discharge tray for storing documents coming from the reading station, a first transport roller disposed at a front position in the transport direction of the reading station, a second discharge roller disposed at a back position in the transport direction of the reading station, a first detection means arranged upstream of the transport roller and a second detection means arranged at a position on the discharge tray side from the point at which the second paired transport rollers contact each other.

Furthermore, the second detection means has a stick-shaped lever member hanging downward that is capable of being swung by an edge of document abutting thereon at a position on the side of the discharge tray from the point at which the second transport rollers contact each other.

DETAILED DESCRIPTION OF PREFERRED EMBODIMENTS

Figure 1:
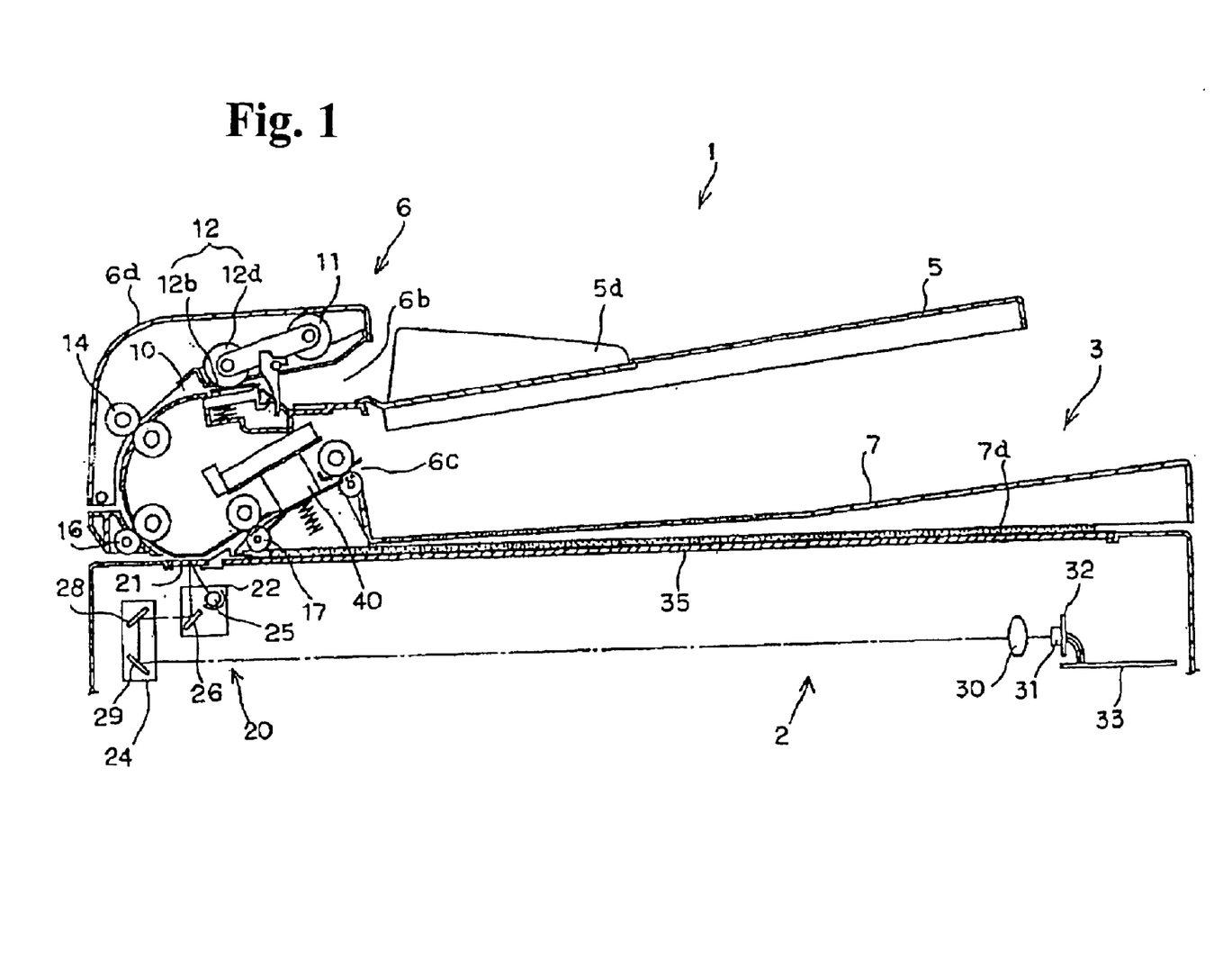
FIG. 1 is a sectional view of an entire automated document feeder apparatus equipped with an image reading apparatus according to the present invention.
Figure 2:
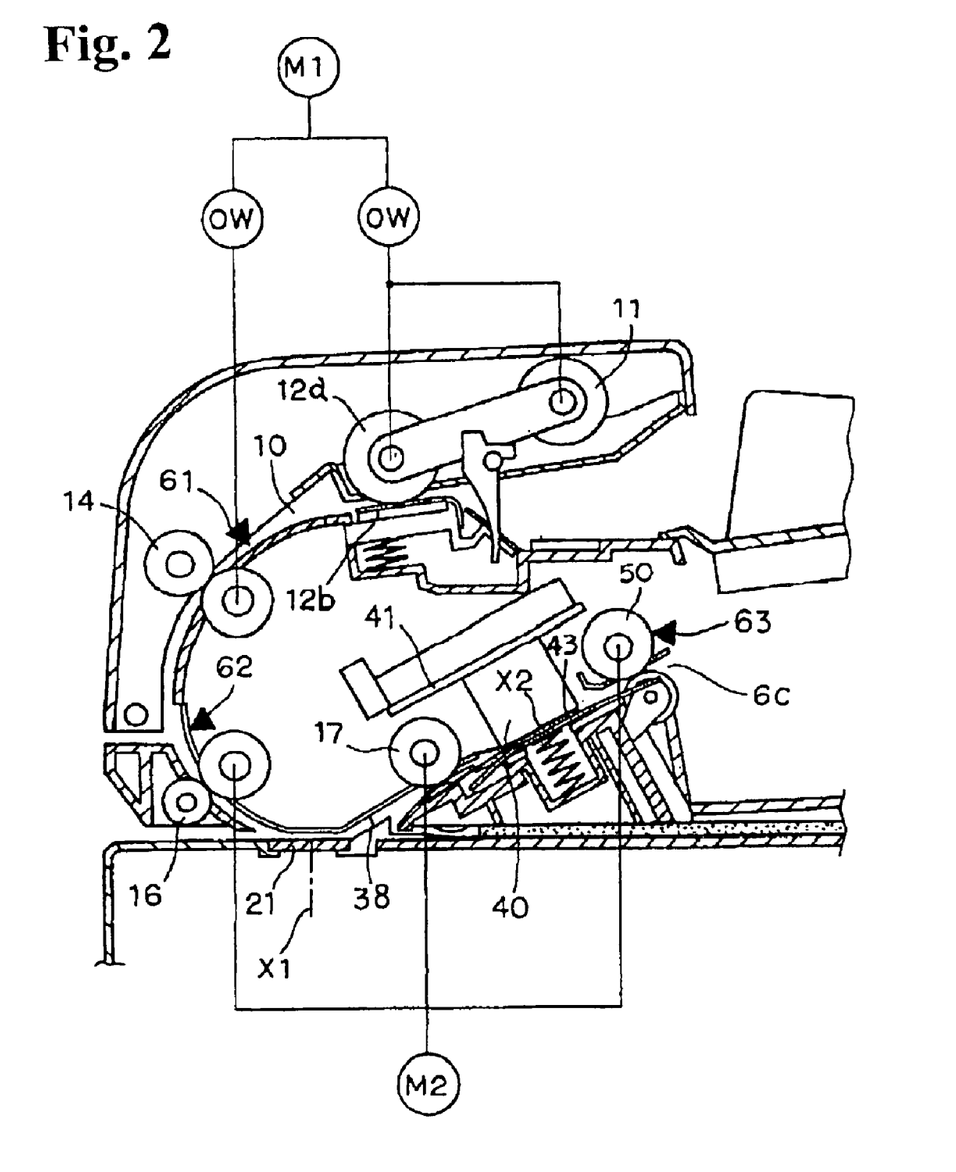
FIG. 2 is an expanded sectional view of the automatic document feeder apparatus shown in FIG. 1.

The following describes in detail embodiments of the present invention according to the accompanied drawings. As an example of the preferred embodiments, FIG. 1 shows an automated document feeder according to the present invention, and FIG. 2 shows the essential parts of the automated document feeder.

According to the present invention, an image reading apparatus operates as a so-called ADF, which continuously pulls out documents and feeds them to an image reading station.

The image reading apparatus 1 has the lower unit 2 and the upper unit 3 mounted to the lower unit 2 by a hinge so that it can be opened and closed.

The upper unit 3 is provided with a sheet supply tray 5 for storing documents in stacks, a main unit 6 that transports documents from the sheet supply tray 5 and reads images on the documents, a paper supply tray, and a discharge tray 7 to which processed documents are discharged. In addition, documents stacked in the sheet supply tray 5 are arranged along the width direction by the paper guide 5a that forms a wall of the document paper feed path.

As is described in further detail below, an image reading apparatus of the present invention has a frame 6a that holds the transport path for transporting documents, a pair of rollers for transporting documents, and an optical reading apparatus for reading images on the documents. To the frame 6a are formed the document inlet 6b corresponding to the sheet supply tray 5, and the document outlet 6c corresponding to the discharge tray 7. The document from the document inlet 6b is transported along the substantially U-shaped transport path 10 that is disposed inside the frame. After the images on the document are read, the document is discharged to the discharge tray 7 via the document outlet 6c.

To the document inlet 6b on the frame 6a is provided a pick-up roller 11 that touches a document stacked in the sheet supply tray 5 and pulls the document out. At downstream of this pickup roller 11 is arranged a paper separation mechanism 12 that comprises a separation pad 12b that touches a separation roller 12a to achieve reliable separation of the pullout documents into a single sheet. At downstream of the transport path in the paper separation mechanism 12, a pair of register rollers 14 is arranged. The edge of the document separated by the paper separation mechanism forms a bend thereby removing any skews thereof.

The reading station of the image reading apparatus according to the present invention is configured with two optical reading means to read images on both sides of a document.

Of these, the first photoelectric conversion means 20 is housed in the lower unit 2, and reads the images on the documents that pass over the sheet-through platen 21 positioned between a pair of read rollers 16 arranged in continuation along the transport path 10 and intermediate rollers 17. The first photoelectric conversion means 20 comprises a reduction sensor and is equipped with the first carriage 22 and the second carriage 24. Each of the carriages 22 and 24 driven by a motor (not shown in the drawings) moves in the left and right directions of the drawing in unison while keeping a specific distance with each other.

On the carriage 22 are mounted the light source 25 for illuminating the document and the reflecting mirror 26 for receiving light reflected from the document illuminated by the light source 25 and changing the direction to a horizontal direction. On the carriage 24 are mounted a reflective mirror 28 to reflect the horizontally directed light from the reflective mirror 26 to a vertical direction, and a reflective mirror 29 that changes the direction of the vertically directed light by the reflective mirror 28 to a horizontal direction that is opposite to that of the light reflected from the reflective mirror 26.

The first photoelectric conversion means 20 is disposed inside the lower unit 2, and comprises a light collecting lens 30 for collecting light from the reflective mirror 29, and the CCD image sensor 31 that receives collected light from the light collecting lens 30. Light detected by this CCD image sensor 31 is converted to digital signal by a CCD circuit board 32, and the signal is then transmitted to an interface printed circuit board in a copier via a control circuit board (not shown in the drawings) which operates various imaging processes.

According to this embodiment of the present invention, the first photoelectric conversion means 20 is configured so that a thick document such as a book can be placed and read. Specifically, a reading station (hereinafter referred to as a book platen) 35 for placing thick documents is disposed above the lower unit 2 adjacent to the sheet through platen 21. The carriages 22 and 24 scan and read the contents of the documents placed on this book reading station. For this reason, to the lower surface of the discharge tray 7 is fastened with an elastic member 7a for pressing documents placed on the book platen 35.

The second photoelectric conversion means 40 is disposed inside the upper unit 3 for reading images on the opposite side of the documents read by the first photoelectric conversion means 20. The second photoelectric conversion means 40 is arranged at downstream of the pair of intermediate rollers 17 where the transport path on the upstream side of the discharge tray forms a straight line. A lifting guide 38 lifts documents passed through a reading position x1 on the sheet-through platen 21, and then the second photoelectric conversion means 40 reads the images on the opposite sides of the document.

According to the present invention, the second photoelectric conversion means 40 comprises a CIS type image sensor. More specifically, it comprises a light source to irradiate light to an image on a document, a protective glass through which this irradiating light and the light reflected from the document pass, and a contact image sensor (CIS) unit holding the image sensor that detects the light reflected from the document that passes through the protective glass. Light detected by the line image sensor is converted into digital signals by a printed circuit board 41, and the digital signal is transmitted to an interface printed circuit board in a copier via an image processing circuit board 33.

The following section explains in detail the configuration of the reading guide means in the second photoelectric conversion means.

Figure 4:
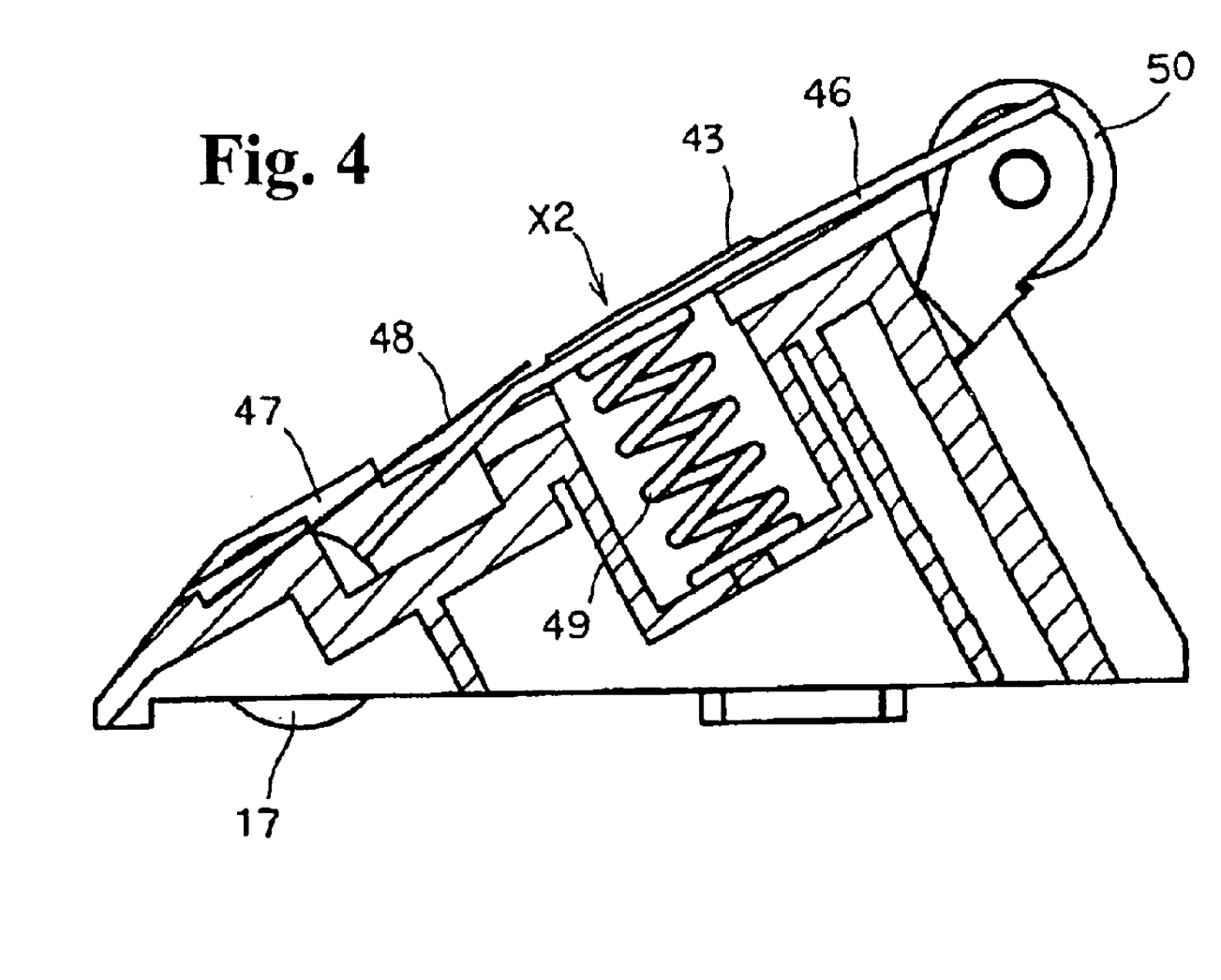
FIG. 4 is an expanded sectional view of the essential portion of the reading transport path in the second reading station of the automatic document feeder apparatus shown in FIG. 2.

FIG. 4 is an expanded sectional view showing the essential portion of reading transport path relating to the second photoelectric conversion means 40. A contact image sensor (CIS) is used in the second photoelectric conversion means 40. As mentioned before, the CIS has a smaller focus depth compared to that of the image reduction optical system, so it is essential to ensure that documents travel in close proximity to the reading surface and in a stable manner. To that end, the space of the document transport path in this reading station is set to be narrow. Also, in order to feed documents smoothly in such a narrow transport path, it is preferred that the CIS is arranged such that the alignment of the transport path be formed in a straight line. According to the preferred embodiment of the present invention, the CIS as the second photoelectric conversion unit 40 is disposed at a position where the upstream transport path of the discharge tray 7 forms a straight line and at downstream of the pair of intermediate rollers 17.

In this way, after reading one side of the document by the first photoelectric conversion means 20, the document is guided to the transport guide 47 and transported to the reading position x2 on the second photoelectric conversion means 40. Then, the other side of the document is read by the second photoelectric conversion means 40.

The reading position x2 on the second photoelectric conversion means 40 is provided with the backup guide 46 which is equipped with the pressure means 49 such as a spring, etc., to press the document against the reading means side to hold the document within a narrow tolerance of the focus depth of the second reading device.

The backup guide 46 is supported in a floating state via the pressure means 49, while the transport guide 47 is fixed on the apparatus chassis. Therefore, a step is created where the transport guide surface and the backup guide surface meet.

When the backup guide surface in the traveling surface of the document protrudes in the traveling surface more than the transport guide, the level will cause jams when a document is a thin sheet. Conversely, when the backup guide surface is lower with regard to the transport guide surface, the shock from the trailing edge of the document passing the step would cause distortion in the reading of the image.

To prevent this from happening, a reading guide 48 for guiding the document from the transport guide 47 to the backup plate 43 is provided. Therefore, the reading guide 48 is an adjustable part depending on the step generated between the transport guide 47 and the backup guide 46. So, it is preferred to form the reading guide means 48 of a bendable filling member. One end of the reading guide 48 is mounted to the transport guide 47 and protrudes from the document transport surface on the transport guide 47 into the circumference of the intermediate rollers 17. The backup guide means 46 is formed of a reference white plate for adjusting shade.

The other end of the reading guide 48 extends up to the image reading position, and eliminates the step between both guides by bending to the backup guide surface moving relative to the transport guide surface. Additionally, the backup plate 43 and the backup guide 46 are supported by a spring so that they can slide along the direction of document transport to enlarge the adjustable range.

Figure 5:
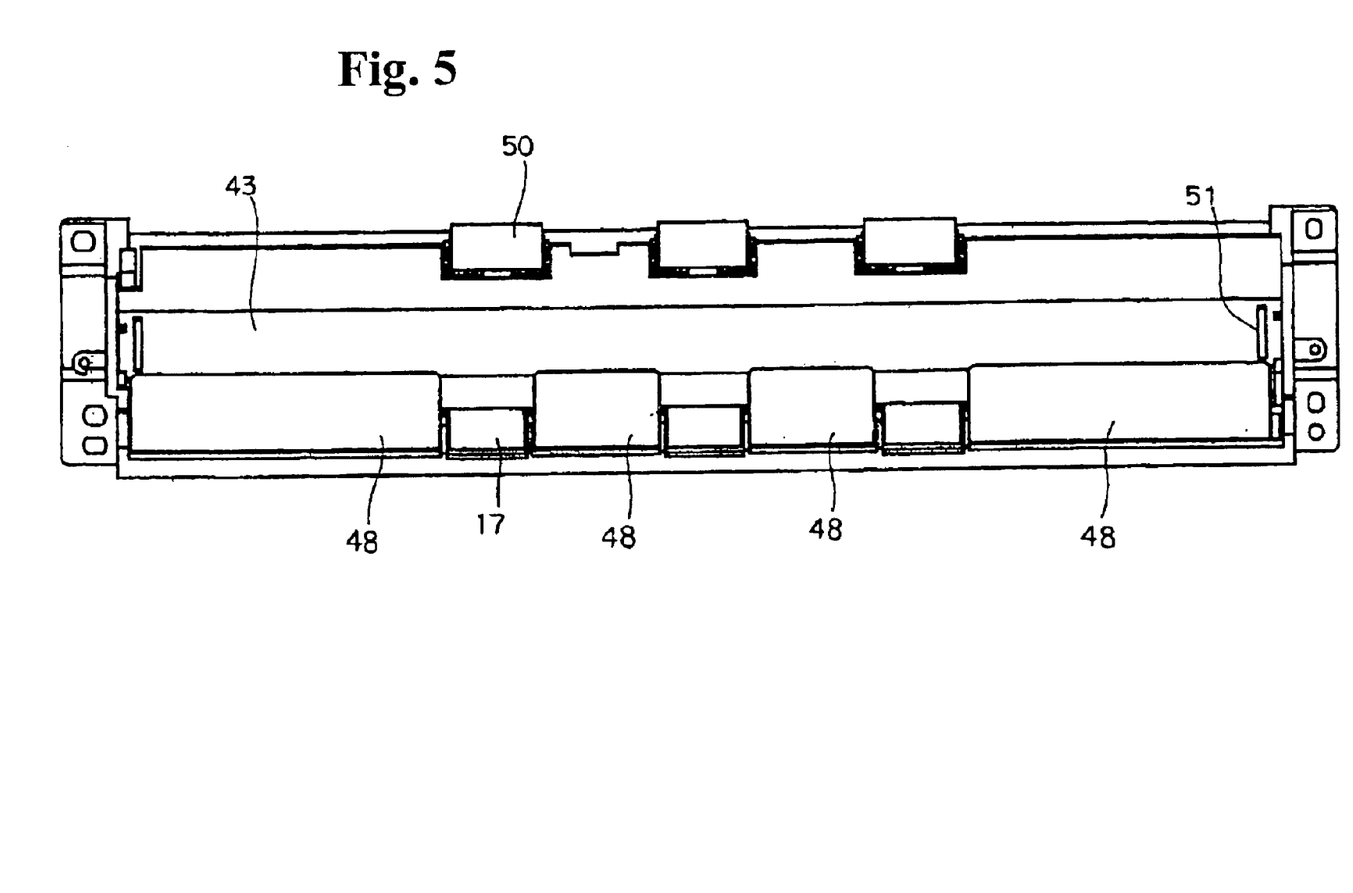
FIG. 5 is a plan view of the reading transport unit shown in FIG. 3.

FIG. 5 is a top plan view of the backup guide portion of the second photoelectric conversion means 40 shown in FIG. 4. The reading guide means 48 is separated and disposed into four pieces sandwiching the intermediate rollers 17 in order to eliminate a step between the transport guide 47 and the backup guide means 46. Also, the protrusion 51 is formed to maintain a gap between the document sheet and the second photoelectric conversion means 40. This protrusion 51 controls the backup guide means 46, which is pressed by the spring guide 49 on the reading guide means 48, to be smaller than a specific gap.

Figure 3:
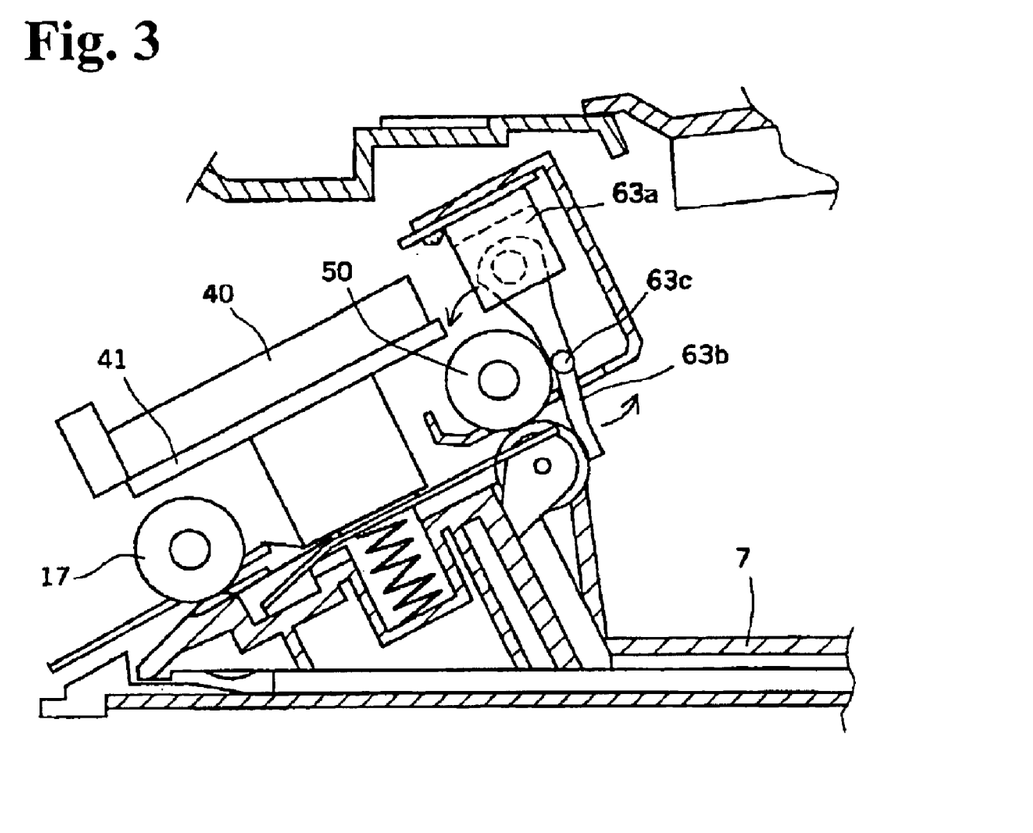
FIG. 3 is a detailed sectional view of the discharge unit on the automatic document feeder apparatus shown in FIG. 1.

At the downstream side of the second photoelectric conversion means 40 as shown in FIG. 3, a pair of discharge rollers 50 is arranged. The pair of discharge rollers discharges processed documents to the discharge tray 7 via the document discharge outlet 6c. Furthermore, according to this embodiment, the discharge rollers 50 contact with each other and extend for a length same as the reading width of the image sensors or longer in their rotational axes direction as a fastened single body. They are configured to prevent the infusion of external light disturbance to the reading line x2 on the photoelectric conversion means 40 through the document discharge outlet 6c. Thus, even if the optical reading device is composed of a CIS which is sensitive to light disturbances, such disturbance is suppressed so that no noise is generated in the analog signal detected by the CCD sensor, and accurate image processing is achieved.

Also, this embodiment of the present invention employs a lever type sensor as a discharge sensor 63 to detect the edge of document, as can be seen in FIG. 3. This discharge sensor 63 is disposed downstream of the discharge rollers 50, or the outlet 6c, so that a shock created by the edge of the document abutting the detection lever 63b, described below, does not affect the quality of processed images on the document.

This discharge sensor 63 comprises a sensor unit 63a, which has a light emitting unit and a light reception unit, and the detection lever 63b, which has one end dangled below the discharge outlet 6c and the other end interrupting the path of light from the light emitting unit to the light reception unit on the sensor unit 63a. While nipped by the pair of read rollers 16, the pair of intermediate rollers 17, and the pair of discharged rollers 50, the document hits one end of the detection lever 63b thereby swinging in the direction of the arrow in FIG. 3 around the pivot point of the sensor pin 63c. This, then, causes the other end of the detection lever 63b to interrupt light from the light emitting unit of the sensor unit 63a so that light can be received at the light reception unit, thus the edge of the sheet is detected.

If a reflective type sensor method is employed as the discharge sensor 63, the pair of discharge rollers 50 would interrupt the light emitted from the light source of the reading means, so the sensors would not fail to detect.

However, according to the preferred embodiment of the present invention, the reflective type sensor can not detect the document if the light emitting unit, light reception unit, or the reflective plate has dirt sticking thereto, hence the lever type sensor method is applied otherwise periodic maintenance is required.

The transport means and the discharge means are driven by two drive motors (not shown in the drawings). The first motor M1 drives the paper feed means, and the second motor M2 drives the transport means and the discharge means. By separating these drive systems, even if a sudden load is applied to the first motor in the cases of separating documents, feeding paper or stopping, the document transportation is maintained stable as the second motor drives the document on the reading station of the second reading apparatus.

Note that, as is shown in FIG. 2, in addition to the discharge sensor 63, a register sensor 61 and a read sensor 62 are disposed to the transport path 10 to detect documents. Based on detection signals from these sensors, the control means (not shown in the drawings) controls the motor that drives the register rollers 14, the read rollers 16, the intermediate rollers 17 and the discharge rollers 50.

Also, the read sensor 62 detects the leading edge of the documents, and initiates adjustments of the movement of the carriages 22 and 24, the reading start timing of each photoelectric conversion means 20 and 40, and flashing of the light source.

Figure 6:
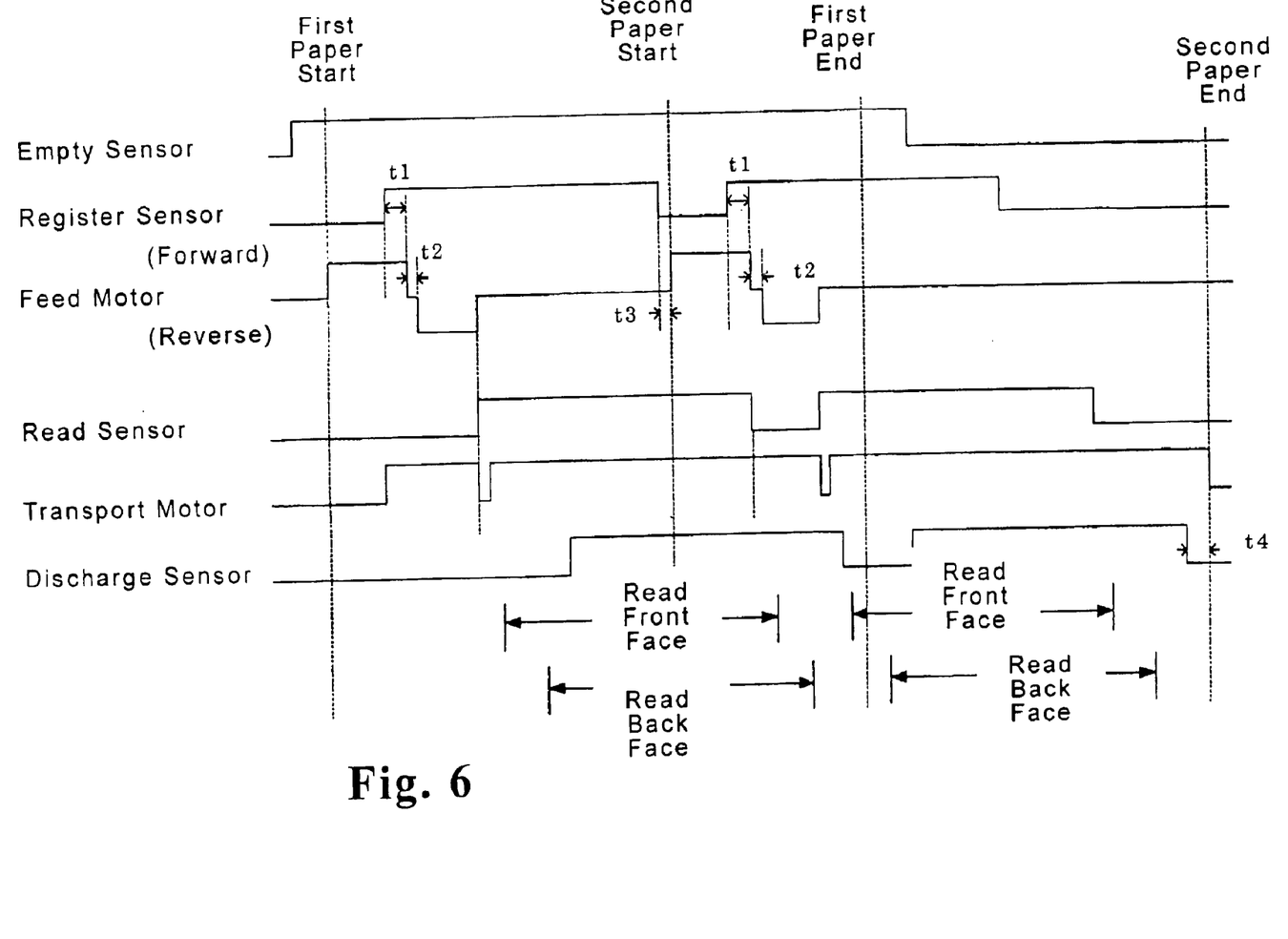
FIG. 6 is a timing chart to explain the sensors on the automatic document feeder apparatus and the drive motor control.

FIG. 6 is an example of the timing chart of each sensor and each motor while reading a document.

In FIG. 1 and FIG. 2, when an empty sensor (not shown in the drawings) detects documents placed on the sheet supply tray and there is an instruction to read documents, the paper feed motor starts to feed a document one at a time by forward rotation. After the documents is fed and the register sensor 61 detects the edge of the first document, the paper feed motor continues to rotate for a determined amount of time (t1) so that the edge of the document sheet abuts the register rollers 14 and bends. After stopping the forward rotation, the paper feed motor starts to rotate in reverse after a determined time (t2), and drives the register rollers 14 to send the first document downstream. At the same time that the read sensor 62 detects the edge of the first document, the paper feed motor stops. The transport motor continues to rotate only for a specified time after the read sensor 62 detects the edge of the document and then stops. After adjusting the read timing, the document starts to be driven for reading the other side by the first photoelectric conversion means 20. As described above, the first document is transported by the transport motor and the other side of the document is read by the second photoelectric conversion means 40.

If the empty sensor continues to detect the second and more documents stacked on the sheet supply tray while the first document is transported and read, the second document is fed after a predetermined time (t3) after the trailing edge of the first document has passed the register sensor. Thus, the time intervals between the first and second documents can be ensured. Then, the register sensor 61 detects the leading edge of the second document, and the leading edge thereof abuts against the register rollers 14. The paper feed and transportation for the second and subsequent documents are operated in the same manner as the first document. While the second sheet is being fed and transported, the discharge rollers 50 discharge the first document. At that time, after the discharge sensor 63 detects the trailing edge of the first document, it is recognized that the document has been discharged to the discharge tray.

By passing a determined amount of time (t4) after the trailing edge of the second document has been detected by the discharge sensor 63, it is recognized that all documents have the discharge tray 7 and all motors are

What is claimed is:

1. An image reading apparatus for reading images on documents by feeding the documents one at a time, comprising:

a document supply tray for stacking the documents;

a transport path for sequentially feeding the documents on said supply tray;

a reading station to read the images on the documents disposed in said transport path;

photoelectric conversion means for photoelectrically converting the images on the documents moving over said reading station;

a discharge tray for storing the documents that have been read from said reading station;

a first transport roller disposed in front and second transport rollers disposed at back relative to the reading station in a direction of transport of the documents, wherein said second transport rollers are paired rollers contacting each other and arranged adjacent to said discharge tray;

first detection means that detects a leading edge of the document and controls start of reading of the document on said reading station, said first detection means being disposed upstream of said first transport roller; and second detection means that detects a trailing edge of said document and detects transport of the document out to said discharge tray, said second detection means being provided with a stick-shaped lever member that abuts against the leading edge of the document at a side of the discharge tray from a contact point of the second transport rollers.

2. An image reading apparatus according to claim 1, wherein said photoelectric conversion means comprises, first photoelectric conversion means for reading the images on one side of the document, and second photoelectric conversion means for reading the other side of the document spaced from the first photoelectric conversion means in the direction of transport of the document, a focus depth of said second photoelectric conversion means being smaller than that of said first photoelectric conversion means.

3. An image reading apparatus according to claim 2, wherein said first photoelectric means is composed of an optical reduction reading sensor and said second photoelectric means is composed of a contact image sensor.

4. An image reading apparatus according to claim 2, wherein said reading station comprises a first reading station for reading one side of the document using said first photoelectric conversion means and a second reading station for reading the other side of the document using said second photoelectric conversion means, and a third reading station is established to stack a document adjacent to said first reading station, at least one of parts of said first photoelectric conversion means moving to read the document placed stationary upon said third reading station.

5. An image reading apparatus according to claim 1, wherein said photoelectric conversion means comprises, first photoelectric conversion means disposed at the reading station for reading the images on one surface of the document in said reading station; and second photoelectric conversion means for reading the other side of said document spaced in the direction of transport of the document from the first photoelectric conversion means by a predetermined distance, said first detection means controlling a start of the first photoelectric conversion means and the second photoelectric conversion means.

6. An image reading apparatus that automatically feeds documents stacked on a sheet supply tray one at a time and discharges the documents to a discharge tray after reading the images on the documents, comprising:

paired transport rollers to transport the documents;

paired discharge rollers to discharge the documents from said paired transport rollers to said discharge tray, said paired discharge rollers being disposed at a downstream side of said paired transport rollers;

a reading station for reading the images on the documents arranged between said paired transport rollers and said paired discharge rollers;

photoelectric conversion means for photoelectrically converting the images on said documents moving over said reading station; and detection means for detecting the documents discharged to said discharge tray by said discharge rollers disposed at a downstream side in a direction of discharge of the documents where said discharge rollers contact each other, said detection means having a stick-shaped lever member hanging downwardly to the discharge tray at a discharge outlet to be swung by a leading edge of the document discharged to the discharge tray, and sensor means for detecting the document by swinging of the lever member.

7. An image reading apparatus according to claim 6, wherein said reading station comprises a transparent glass to guide the document read by said reading means, and an document guide path comprising a guide member facing said transparent glass.

* * * * *